(12) United States Patent
Wheeler et al.

(10) Patent No.: US 11,385,400 B2
(45) Date of Patent: Jul. 12, 2022

(54) FLEXIBLE OPTICAL WAVEGUIDES AND METHODS FOR MANUFACTURING FLEXIBLE OPTICAL WAVEGUIDES

(71) Applicant: The Charles Stark Draper Laboratory, Inc., Cambridge, MA (US)

(72) Inventors: Jesse J. Wheeler, Revere, MA (US); Joseph J. Register, Cambridge, MA (US); Parshant Kumar, Cambridge, MA (US); Carlos A. Segura, Cambridge, MA (US); Charles A. Lissandrello, Cambridge, MA (US); John J. LeBlanc, Cambridge, MA (US)

(73) Assignee: The Charles Stark Draper Laboratory, Inc., Cambrige, MA (US)

( * ) Notice: Subject to any disclaimer, the term of this patent is extended or adjusted under 35 U.S.C. 154(b) by 0 days.

(21) Appl. No.: 15/811,203

(22) Filed: Nov. 13, 2017

(65) Prior Publication Data
US 2018/0136389 A1     May 17, 2018

Related U.S. Application Data

(60) Provisional application No. 62/421,785, filed on Nov. 14, 2016.

(51) Int. Cl.
*G02B 6/02*     (2006.01)
*A61B 5/00*     (2006.01)
(Continued)

(52) U.S. Cl.
CPC ........ *G02B 6/02033* (2013.01); *A61B 5/6846* (2013.01); *A61N 5/0601* (2013.01); *B05D 1/005* (2013.01); *B05D 3/107* (2013.01); *B05D 3/12* (2013.01); *G02B 1/046* (2013.01); *G02B 1/048* (2013.01); *G02B 6/12* (2013.01); *G02B 6/262* (2013.01); *A61N 2005/0612* (2013.01);
(Continued)

(58) Field of Classification Search
CPC ... A61L 33/00; G02B 6/02033; A61B 5/6846; A61B 5/0478
USPC ......................................................... 427/184
See application file for complete search history.

(56) References Cited

U.S. PATENT DOCUMENTS

| 2008/0031584 | A1* | 2/2008 | Payne ..................... | G02B 6/136 385/132 |
| 2011/0112591 | A1* | 5/2011 | Seymour .............. | A61B 5/0084 607/3 |

FOREIGN PATENT DOCUMENTS

| WO | WO-03/021313 A1 | 3/2003 |
| WO | WO-03/025644 A1 | 3/2003 |

(Continued)

OTHER PUBLICATIONS

E1, Photolithography, Jul. 2020, Wikipedia, https://en.wikipedia.org/wiki/Photolithography.*
(Continued)

*Primary Examiner* — Dah-Wei D. Yuan
*Assistant Examiner* — Andrew J Bowman
(74) *Attorney, Agent, or Firm* — Foley & Lardner LLP

(57) ABSTRACT

The material stack of the present disclosure can be used for fabricating optical waveguides that are thin and flexible, and that can bend light around small turns. The stack of materials can include a polymer core and a cladding, which together can create a large difference in refractive index. As a result, light can remain within the core even when bent around radii where standard glass fibers could fail.

19 Claims, 4 Drawing Sheets

(51) Int. Cl.
*G02B 6/12* (2006.01)
*A61N 5/06* (2006.01)
*B05D 1/00* (2006.01)
*B05D 3/10* (2006.01)
*B05D 3/12* (2006.01)
*G02B 1/04* (2006.01)
*G02B 6/26* (2006.01)

(52) U.S. Cl.
CPC .............. *G02B 2006/12069* (2013.01); *G02B 2006/12138* (2013.01)

(56) References Cited

FOREIGN PATENT DOCUMENTS

| WO | WO-2003025644 | * | 10/2003 | ........... A61B 5/0084 |
| WO | WO-2012/135511 A1 | | 10/2012 | |
| WO | WO-2012135511 A1 | * | 10/2012 | ........... A61B 5/0084 |

OTHER PUBLICATIONS

International Search Report and Written Opinion for PCT/US2017/061378 dated Feb. 21, 2018.
International Preliminary Report on Patentability, Ch. I, for PCT Appln. Ser. No. PCT/US2017/061378 dated May 23, 2019 (8 pages).
Examination Report on EP 17804774.2 dated Mar. 16, 2021.
Storage and Preparation Tank Design Technical Bulletin, Jul. 1, 2003, pp. 1-2, retrieved from the internet, www.actontech.com.

* cited by examiner

FLEXIBLE OPTICAL WAVEGUIDES AND METHODS FOR MANUFACTURING FLEXIBLE OPTICAL WAVEGUIDES

CROSS-REFERENCE TO RELATED APPLICATION

This application claims priority to U.S. Provisional Patent Application No. 62/421,785 filed on Nov. 14, 2016 and titled "Flexible Optical Waveguides and Methods for Manufacturing Flexible Optical Waveguides," which is herein incorporated by reference in its entirety.

BACKGROUND OF THE DISCLOSURE

The field of optogenetics generally relates to sensitizing target neurons to light stimuli. For example, this can be achieved by inserting light-sensitive opsins using genetic techniques. After the target neurons have been sensitized to light, light pulses can be delivered to the target neurons to stimulate the target neurons. Typically, target neurons may be very small and may be surrounded by soft tissue. Thus, it can be difficult to bend and route light in a manner to introduce light stimuli to the neurons.

SUMMARY OF THE DISCLOSURE

According to an aspect of the disclosure, a method to manufacture an implantable optrode can include depositing a first cladding layer that can include a fluoropolymer. The method can include treating the first cladding layer with a fluoropolymer etchant. The etchant can change a surface energy of a first face of the first cladding layer. The method can include depositing a core material on the first face of the first cladding layer. The method can include encapsulating the core material with a second cladding layer.

In some implementations, the core material can include poly(methyl methacrylate). The change to the surface energy of the first face of the first cladding layer can enable the core material to bond with the first cladding layer.

The method can include etching the core material to form a waveguide. The waveguide can have a width between about 10 µm and about 1 mm. The waveguide can have a thickness between about 10 µm and about 1 mm. The waveguide can have at least one turn with a diameter between about 250 µm and about 1000 µm.

The method can include depositing a release layer onto a silicon wafer. The method can include depositing a planar or mesh substrate layer on the release layer for mechanical support or electrical isolation. The substrate layer can include polyimide or parylene. The substrate layer can be between about 10 µm and about 30 µm.

The method can include depositing a resist layer on the substrate layer. The method can include patterning the resist layer. The method can include depositing a metal layer on the resist layer. The method can include removing the resist layer to form at least one electrode and at least one contact pad.

The first cladding layer can at least partially encapsulate the metal layer. The method can include drilling through the first cladding layer and the second cladding layer to expose a portion of the metal layer to an external environment. The method can include drilling through the substrate layer to expose a portion of the metal layer to the external environment.

The metal layer can include at least one of chromium, gold, platinum, tungsten, or titanium. The method can include depositing a second metal layer on the metal layer. The metal layer can be between about 100 nm and about 5 µm thick.

In some implementations, the first cladding layer can include at least one of Cytop or Cyclotene. The first cladding layer can be between about 2 µm and about 10 µm thick. The method can include forming a plurality of waveguides in core material. The method can include thermally planerizing the second cladding layer.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Following below are more detailed descriptions of various concepts related to, and implementations of flexible optical waveguides and methods for manufacturing flexible optical waveguides. The waveguides can be used in optogenetic optrodes, light stimulation devices, imaging devices, and other types of optrodes. The various concepts introduced above and discussed in greater detail below may be implemented in any of numerous ways, as the described concepts are not limited to any particular manner of implementation. Examples of specific implementations and applications are provided primarily for illustrative purposes. As described above, the field of optogenetics can benefit from devices that can be configured to route light around tight turns in order to access small anatomical targets, such as targeted neural tissue. Traditional optical fibers can be efficient at transmitting light across distances, but are limited in their ability to bend light around small diameter turns, such as turns having a diameter of less than one millimeter. For example, the turn can have a diameter between about 50 µm and about 1000 µm, between about 250 µm and about 1000 µm, or between about 500 µm and about 1000 µm. This disclosure describes a novel material stack that can be used for fabricating optical waveguides that are thin and flexible, and that can bend light around such small turns.

Figure 1:
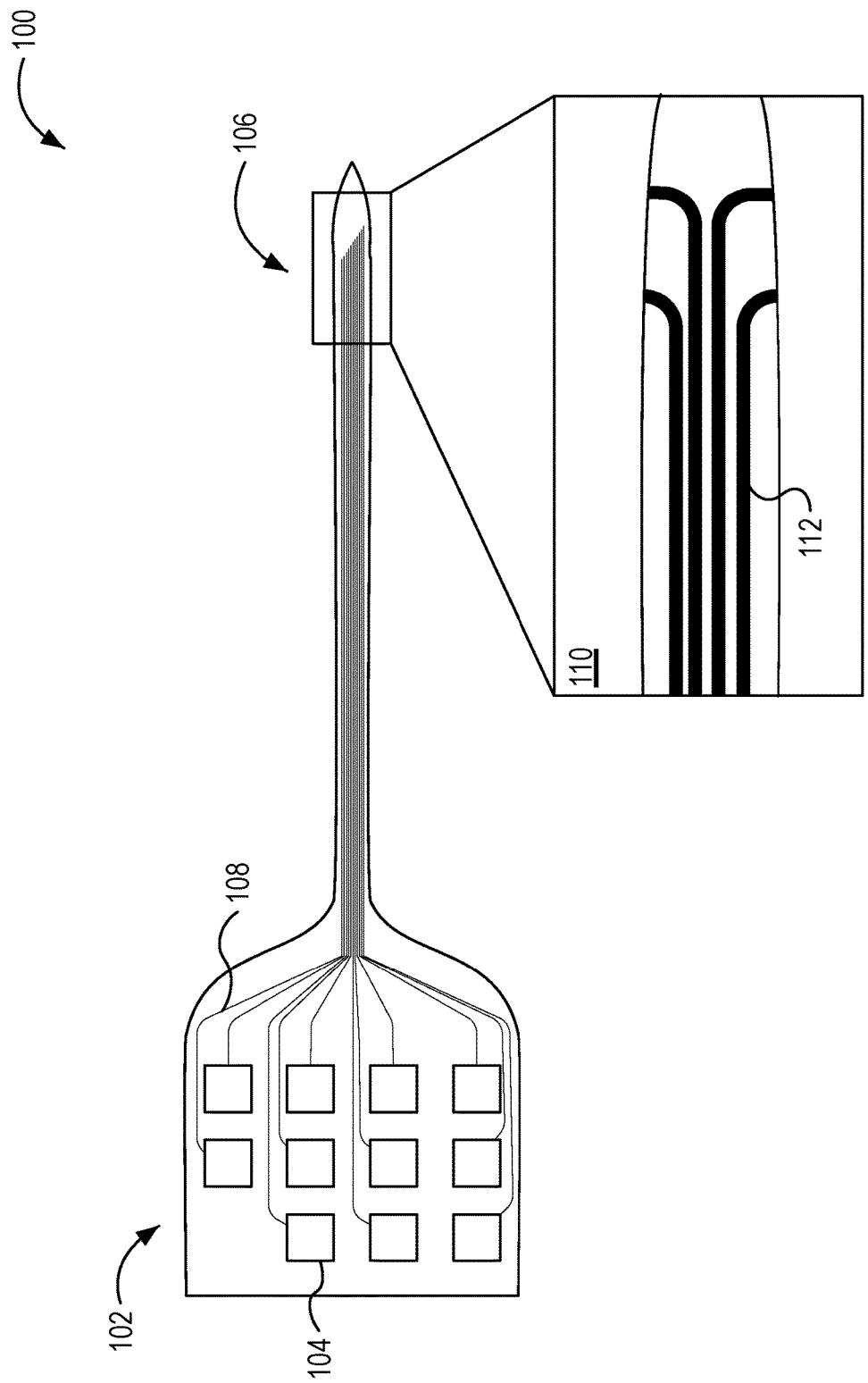
FIG. 1 illustrates a schematic of an example optrode.

FIG. 1 illustrates a schematic of an example optrode 100. A proximal end 102 of the optrode 100 includes a plurality of contact pads 104. Each of the contact pads 104 can be electrically coupled to an electrode site at the distal end 106 of the optrode 100 through an electrical trace 108. The enlarged portion 110 of the distal end 106 illustrates the optrode 100 also includes a plurality of optical waveguides 112 (which can also be referred to as waveguides 112).

The waveguides 112 can carry or transmit light from the proximal end 102 to the distal end 106 (in cases of projecting light from the distal end 106) or from the distal end 106 to the proximal end 102 (in cases of detecting light from the distal end 106).

As further described in relation to FIGS. 2A-2L, the optrode 100 can include a stack of materials where the waveguides 112 are formed from a polymer core and a cladding. The polymer core and the classing, together, create a large difference in refractive index. As a result, light can remain within the core (e.g., the waveguide 112) even when bent around radii where standard glass fibers could fail.

As described further below, the materials of the optrode 100 can be patterned using, for example, photolithographic methods and can be integrated with other types of structures, such as microfluidic structures or electrical structures (e.g., the contact pads 104 and electrical traces 108). In some implementations, the microfabricated waveguides 112 may be thin and flexible to enable the waveguides 112 to easily bend and wrap around small structures without a substantial loss of light along the length of the waveguide 112. For example, traditional optical fibers may be unable to bend light around turns that are smaller than a few millimeters. However, the flexible optical waveguides described herein are capable of bending light around turns of less than one millimeter.

The waveguides 112 and below described material stack can enable the optrode 100 to wrap around structures (e.g., soft tissue, nerves, etc.) and maintain robust interfaces with the structures by matching the mechanical properties of the structures. Unlike stiff optical waveguides, the optrode 100 can be a closer mechanical match to the modulus of soft tissue, which can allow the optrode 100 to more robustly integrate with tissue for chronic applications. Flexibility can allow the optrode 100 to bend around tissue structures allowing easier delivery and routing of light through the tissue.

The material stack of the optrode 100 enables light to be bent around very fine structures (e.g., smaller than one millimeter), which can enable the optrode 100 to wrap around tissue, such as small nerves. The optrode 100 can be used to both deliver light and capture light for both stimulation and monitoring applications. In some implementations, stiff mechanical backings and leader (e.g. a needle) can be used for inserting the optrode 100 and can be detached after insertion, leaving behind the optrode 100. The optrode 100 can be combined with optogenetic stimulation and monitoring techniques to selectively activate tissue (e.g. neural, cardiac, etc.). In some implementations, combining optical and electrical modes for stimulation and monitoring can help to minimize undesirable artifacts caused by simultaneous stimulation and monitoring using only a single mode (e.g., only electrical or only optical). Bending and routing light around tight turns can enable both miniaturization of arrays or of the waveguides 112, as well as higher channel counts. In some implementations, the optrode 100 (and the waveguide stack) can have a thickness of between about 15 µm and about 50 µm, between about 25 µm and about 40 µm, or between about 25 and about 35 µm near the distal end 106. The distal end 106 can width between about 50 µm and about 300 µm, between about 100 µm and about 250 µm, or between about 150 µm and about 250 µm.

FIGS. 2A-2L illustrate a method for manufacturing the material stack of the optrode 100 illustrated in FIG. 1. The materials and method described herein can be patterned using, for example, photolithographic methods. The material stack described herein can be integrated with other types of structures, such as microfluidic structures or electrical structures. The optrodes 100 manufactured with the below described method can be thin and flexible and enable the optrode 100 (and the waveguides contained therein) to easily bend and wrap around small structures without substantial light leak.

Figure 2A:
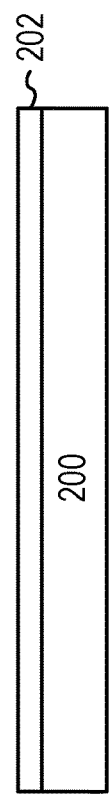
FIGS. 2A-2L illustrate a method for manufacturing the material stack of the optrode illustrated in FIG. 1.

As illustrated in FIG. 2A, a silicon wafer 200 is provided. A release layer 202 is deposited onto the silicon wafer 200. The release layer 202 can be an oxide material and can be deposited to a depth of about 1 µm.

Figure 2B:
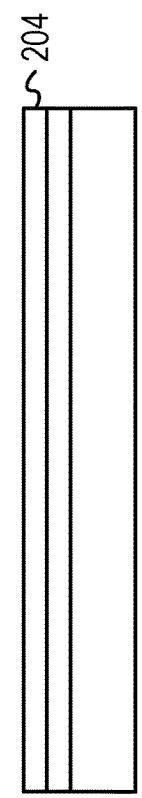

In FIG. 2B, a substrate layer 204 can be deposited onto the release layer 202. The substrate layer 204 can form one face of the optrode 100. The substrate layer 204 can be spin coated onto the release layer 202 to a depth between about 10 µm and about 30 µm, between about 10 and 20 µm, or between about 10 µm and about 15 µm. In some implementations, the substrate layer 204 can include HD4010 photo-patternable polyimide or other type of polyimide. In some implementations, the substrate layer 204 is a mesh substrate layer. The substrate layer 204 can provide mechanical support and/or electrical isolation for the material stack.

Figure 2C:
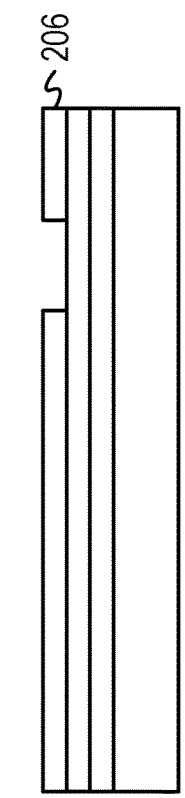
Figure 2D:
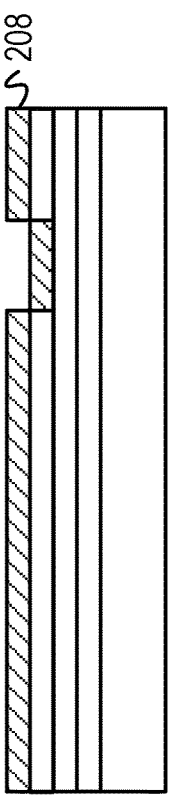

Next, in FIG. 2C, a resist 206 can be spin coated onto the substrate layer 204. The resist 206 can be patterned to form deposition areas for subsequent layers of the material stack. The resist 206 can include a hexamethyldisilazane (HDMS) resist. As illustrated in FIG. 2D, a metal layer 208 can be deposited onto the resist 206. The metal layer 208 can be deposited to a depth of between about 1 µm and about 5 µm, between about 1 µm and about 3 µm, or between about 1 µm and about 2 µm. The metal layer 208 can include one or more conductive metals. The metals can include chromium, gold, tungsten, platinum, titanium, or any combination thereof. In some implementations, a plurality of metals can be successively deposited onto one another such that the metal layer 208 includes a plurality of layered metals.

Figure 2E:
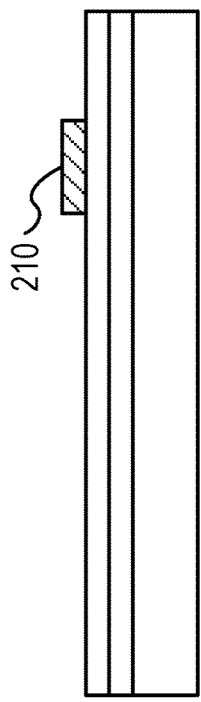

In FIG. 2E, the resist 206 can be removed, leaving a portion 210 of the metal layer 208 on the substrate layer 204. The remaining portion 210 of the metal layer 208 can form a portion of an electrode site, contact pad 104, or electrical trace 108.

Figure 2F:
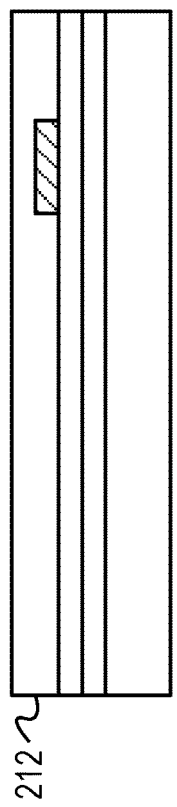

In FIG. 2F, a bottom cladding layer 212 can be deposited. The bottom cladding layer 212 can encapsulate the portion 210 of the metal layer 208. The bottom cladding layer 212 can include Cytop™ (made available by Asahi Glass Company), Cyclotene™ (made available by Dow Chemical), Taflon AF™ (made available by Chemours), or other fluoropolymer. In some implementations, the bottom cladding layer 212 can be applied through spin coating. The bottom cladding layer 212 can be deposited through multiple spin coating applications. The bottom cladding layer 212 can be deposited to a depth (for the total bottom cladding layer 212) of between about 2 µm and about 10 µm, between about 2 µm and about 8 µm, or between about 4 µm and about 6 µm.

Figure 2G:
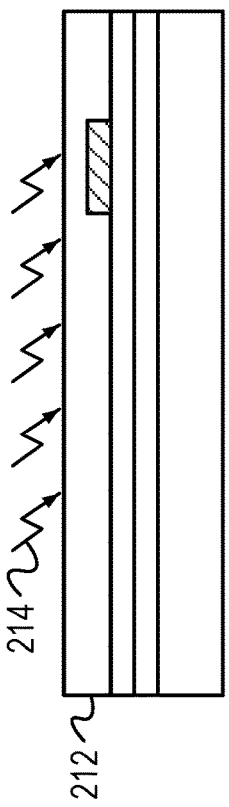

As illustrated in FIG. 2G, an etchant 214 can be applied to the bottom cladding layer 212. The etchant 214 (or other surface treatment) can change the surface energy of the exposed face of the bottom cladding layer 212. The etchant 214 can enable the subsequent layers to better adhere or bond to the bottom cladding layer 212 (or other cladding layers). The etchant 214 can be a fluoropolymer etchant. The etchant 214 can be diglyme-based. For example, the etchant 214 can be FluoroEtch® (made available by Acton Technologies).

Figure 2H:
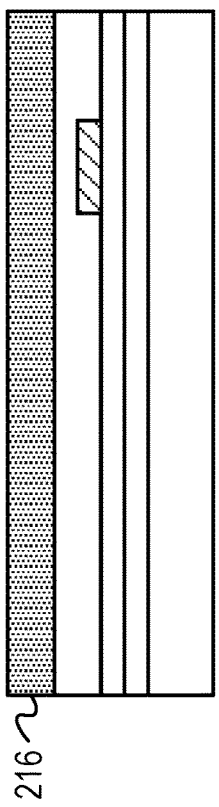

In FIG. 2H, the core material 216 is deposited onto the treated bottom cladding layer 212. The core material 216 can be applied through several spin coatings to form a depth of between about 10 µm and about 50 µm, between about 10 µm and about 40 µm, between about 20 µm and about 30 µm, or between about 25 µm and about 30 µm. The core material 216 can include Ormocore® (made available by Microresist), or poly(methyl methacrylate) (PMMA), SU-8, or poly (p-xylylene) polymers.

Figure 2K:
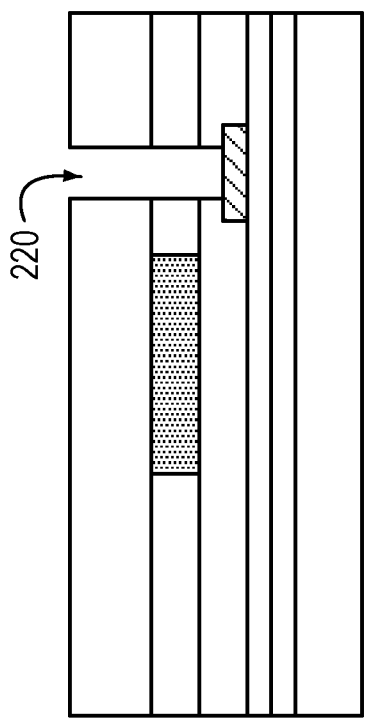
Figure 2L:
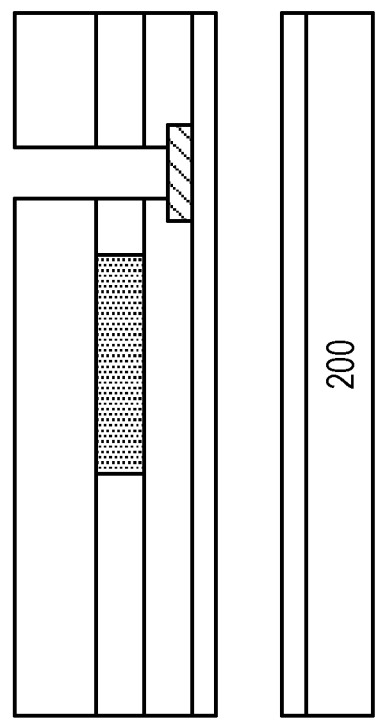
Figure 2I:
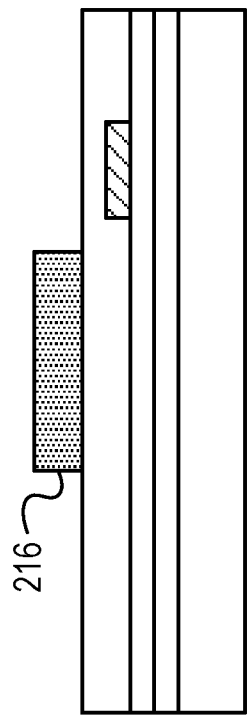

In FIG. 2I, the core material 216 is etched to form the waveguide 112. The core material 216 can be etched with reactive ion etching (RIE). The core material 216 can be patterned, or drilled to from the waveguide 112. In some implementations, the core material 216 (or waveguide 112) can be etched, patterned, or drilled to form geometries in the waveguide 112 that reflect, scatter, or exit light out of plane. The geometries can include dimples, ridges, or angles that are cut into the core material 216. The In some implementations, a reflective layer or mirror coating can be deposited onto the core material 216. In some implementations, the core material 216 is etched such that the waveguide 112 has a width of between about 10 μm and about 1 mm, between about 25 μm and about 500 μm, between about 25 μm and about 250 μm, or between about 25 μm and about 100 μm. In some implementations, the core material 216 is etched such that the waveguide 112 has a thickness of between about 10 μm and about 1 mm, between about 25 μm and about 500 μm, between about 25 μm and about 250 μm, or between about 25 μm and about 100 μm.

Figure 2J:
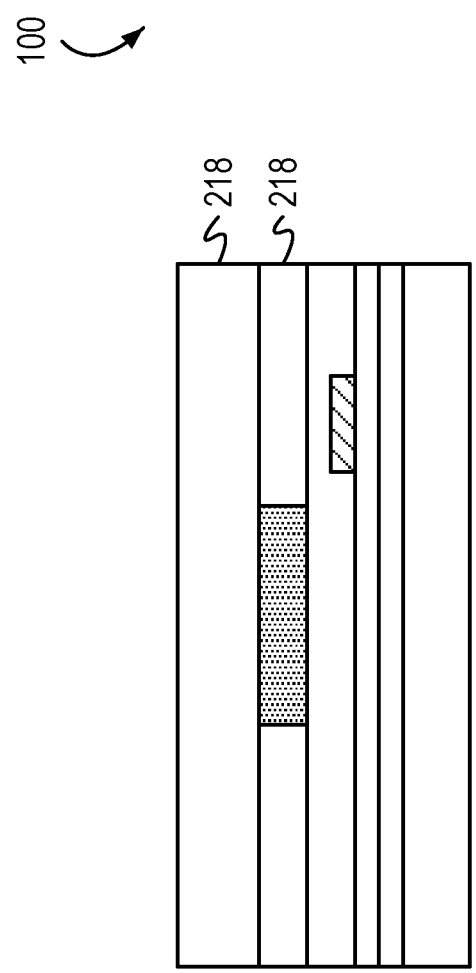

In FIG. 2J, upper cladding layers 218 are deposited onto the core material 216 and the portions of the bottom cladding layer 212 exposed by the core material 216. The upper cladding layers 218 can include the same materials as the bottom cladding layer 212. The upper cladding layers 218 can be applied in multiple spin coating treatments to desired thickness. In some implementations, the upper cladding layer 218 can be thermally planarized in reflow to form a substantially flat surface that can facilitate mounting in subsequent steps.

In FIG. 2K, a hole 220 is drilled through the upper cladding layers 218 and the bottom cladding layer 212 to expose a portion of the metal layer 208 to the external environment. The hole 220 can be etched or otherwise cute through the upper cladding layers 218 and the bottom cladding layer 212. The exposed portion of the metal layer 208 form an electrode to electrically stimulate or record from the surrounding soft tissue. Similarly, portions of the metal layer 208 can be exposed through drilling to form the contact pads 104. The drilling can be performed by laser or micro-drilling. In some implementations, a plurality of optrodes 100 can be formed on a single silicon wafer 200. The material stack can be diced with a resonetics laser to form individual optrodes 100.

In FIG. 2L, the optrode 100 is separated from the silicon wafer 200. The optrode 100 can be lifted off the silicon wafer 200 by dissolving the release layer 202. In some implementations, the material stack can be mounted onto a backing film (or a dicing film) prior to the lift off process. Once mounted to the backing film, the release layer 202 can be dissolved to release the material stack from the silicon wafer 200. In some implementations, the substrate layer 204 can be laser drilled to expose a portion of the metal layer 208 through the substrate layer 204 rather than the cladding layers.

In some implementations, the material stack can include a plurality of waveguides 112. The waveguides 112 can be included in the same layer or can be included in different layers of the material stack. The material stack can also include multiple metal layers 208. In some implementations, the material stack can include a first metal layer 208 for trace routing and a second metal layer 208 that includes the electrode sites and contact pads 104. The different metal layers 208 can be electrically coupled to one another through vias. In some implementations, the material stack can include one or more optical interconnects between different waveguides. In some implementations, one or more channels can be machined into the material stack to form microfluidic channels and microfluidic interconnects. The microfluidic channels can also be formed by embedding tubing or channels into the material stack.

Figure 3A:
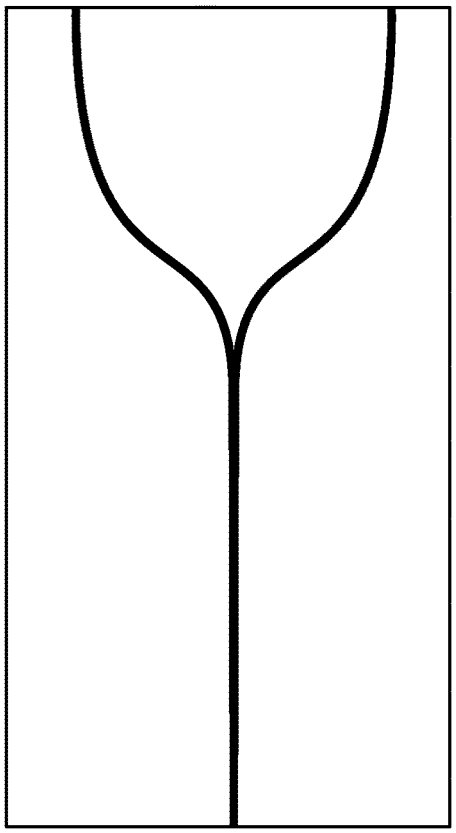
FIGS. 3A-3D illustrate additional waveguide geometries that can be manufactured using the method illustrated in FIGS. 2A-2L.
Figure 3B:
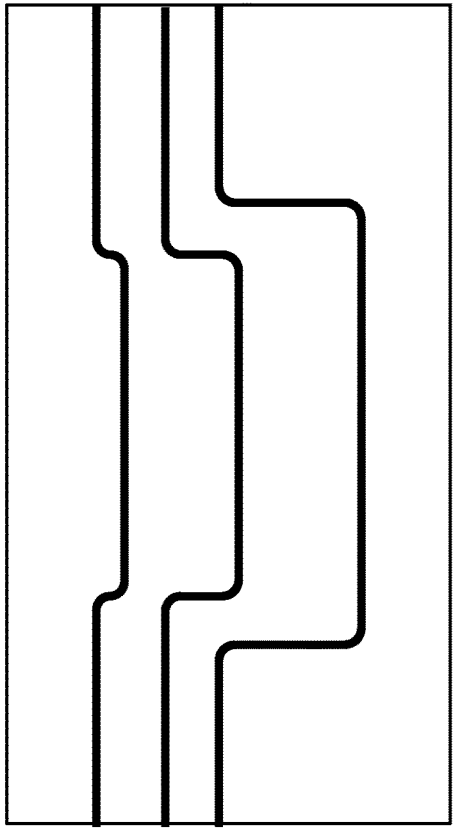
Figure 3C:
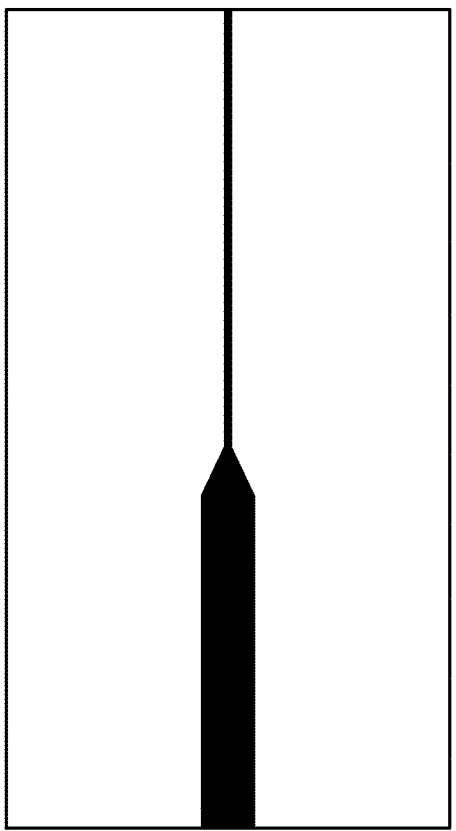
Figure 3D:
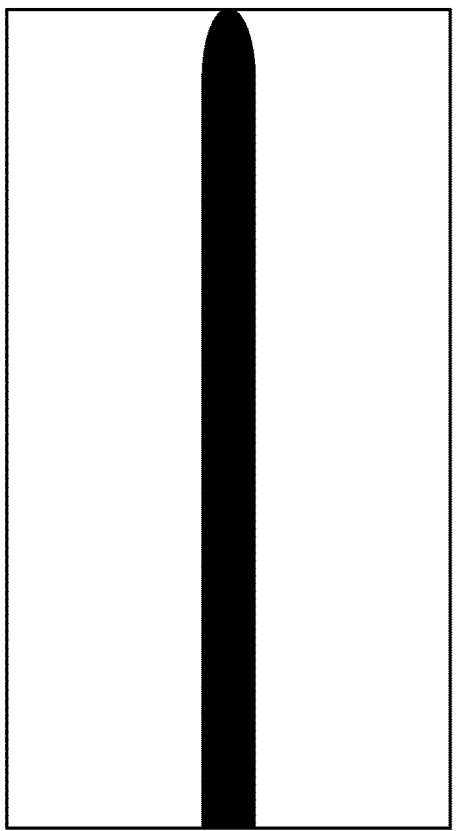

FIGS. 3A-3D illustrate other waveguide geometries that can be manufactured using the above-described material stack. FIG. 3A illustrates an example waveguide slitter 300 that can be used to slit light from a single branch into one or more branches. FIG. 3B illustrates a plurality of curved waveguides 302 that can be used to route light through the optrode 100. FIG. 3C illustrates an example tapering waveguide 304. FIG. 3D illustrates an example lens 306.

CONCLUSION

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A method to manufacture an implantable optrode, comprising:
   depositing a resist layer over a substrate layer;
   patterning the resist layer;
   depositing a metal layer over the patterned resist layer;
   removing the patterned resist layer to form at least one electrode and at least one contact pad;
   depositing a first cladding layer comprising a fluoropolymer such that a first face of the first cladding layer faces towards the substrate layer;
   treating at least a first portion of a second face of the first cladding layer, opposite the substrate layer, with a fluoropolymer etchant to change a surface energy of the second face of the first cladding layer;
   depositing a core material on the at least the first portion of the second face of the first cladding layer;
   encapsulating the core material with a second cladding layer, such that a portion of a first face of the second cladding layer faces towards the substrate layer;
   machining one or more channels into the implantable optrode to form one or more microfluidic channels in the implantable optrode; and
   mounting a second face of the second cladding layer, opposite the first face of the second cladding layer, to a backing film, wherein a portion of the metal layer is exposed to an external environment through the substrate layer responsive to mounting the second face of the second cladding layer to the backing film.

2. The method of claim 1, wherein the core material comprises at least one of poly(methyl methacrylate) (PMMA), SU-8, or parylene.

3. The method of claim 2, wherein the change to the surface energy of the first face of the first cladding layer is configured to enable the core material to bond with the first cladding layer.

4. The method of claim 1, further comprising etching or patterning the core material to form a waveguide.

5. The method of claim 4, wherein the waveguide has a width between about 10 µm and about 1 mm.

6. The method of claim 4, wherein the waveguide has a thickness between about 10 µm and about 1 mm.

7. The method of claim 4, wherein the waveguide comprises at least one turn with a diameter between about 50 µm and about 1000 µm.

8. The method of claim 1, further comprising:
   depositing a release layer onto a silicon wafer; and
   depositing the substrate layer on the release layer.

9. The method of claim 8, wherein the substrate layer is between about 10 µm and about 30 µm.

10. The method of claim 1, wherein the first cladding layer at least partially encapsulates the metal layer.

11. The method of claim 10, further comprising drilling through the first cladding layer and the second cladding layer to expose the portion of the metal layer to the external environment.

12. The method of claim 1, wherein the metal layer comprises at least one of chromium, gold, or titanium.

13. The method of claim 1, further comprising depositing a second metal layer on the metal layer.

14. The method of claim 1, wherein the metal layer is between about 1 µm and about 5 µm thick.

15. The method of claim 1, wherein the first cladding layer comprises at least one of poly(perfluorobutenyl vinyl ether) or 3-Methyl-1,2-cyclopentanedione.

16. The method of claim 1, wherein the first cladding layer is between about 2 µm and about 10 µm thick.

17. The method of claim 1, further comprising forming a plurality of waveguides in the core material.

18. The method of claim 1, further comprising forming, in the core material, one or more of a waveguide slitter, a curved waveguide, a tapering waveguide, or a lens.

19. The method of claim 1, further comprising depositing a second layer of the core material and a third cladding layer to define a second waveguide in the implantable optrode.

* * * * *